US007410583B2

(12) United States Patent
Gray (Gabb) et al.

(10) Patent No.: US 7,410,583 B2
(45) Date of Patent: Aug. 12, 2008

(54) PROCESS OF TREATING ORGANIC WASTE FOR ANAEROBIC DIGESTION

(75) Inventors: Donald M. D. Gray (Gabb), Oakland, CA (US); Paul J. Suto, Walnut Creek, CA (US)

(73) Assignee: East Bay Municipal Utility District, Oakland, CA (US)

( * ) Notice: Subject to any disclaimer, the term of this patent is extended or adjusted under 35 U.S.C. 154(b) by 240 days.

(21) Appl. No.: 11/503,098

(22) Filed: Aug. 10, 2006

(65) Prior Publication Data

US 2008/0035561 A1 Feb. 14, 2008

(51) Int. Cl.
*C02F 11/04* (2006.01)
*C02F 3/28* (2006.01)
*C05F 7/00* (2006.01)

(52) U.S. Cl. .............................. 210/603; 210/609; 71/10
(58) Field of Classification Search ................ 210/603, 210/609, 173, 174; 71/10, 11; 100/110, 100/117
See application file for complete search history.

(56) References Cited

U.S. PATENT DOCUMENTS

| | | |
|---|---|---|
| 4,040,953 A | 8/1977 | Ort |
| 4,185,680 A | 1/1980 | Lawson |
| 4,245,396 A * | 1/1981 | Maffet ......................... 34/386 |
| 4,287,058 A * | 9/1981 | Larsen ........................ 210/112 |
| 4,429,043 A | 1/1984 | Paton |
| 4,503,154 A | 3/1985 | Paton |
| 4,510,243 A | 4/1985 | Haga et al. |
| 4,511,370 A | 4/1985 | Hunziker et al. |
| 4,684,468 A | 8/1987 | De Baere |
| 4,758,344 A | 7/1988 | Wildenauer |
| 4,784,770 A | 11/1988 | Nagao |
| 4,846,975 A * | 7/1989 | Kelyman ...................... 210/603 |
| 5,207,911 A | 5/1993 | Pellegrin et al. |

(Continued)

FOREIGN PATENT DOCUMENTS

JP 2002-336825 A * 11/2002

(Continued)

OTHER PUBLICATIONS

Brown International Corp. "Model 202 Pulper Finisher De-Waterer Separator." Brown International Corporation (Aug. 2006).

(Continued)

*Primary Examiner*—Fred Prince
(74) *Attorney, Agent, or Firm*—James R. Cypher

(57) ABSTRACT

A process of treating organic waste such as food wastes for anaerobic digestion including preparing a waste-slurry from organic waste such as food wastes, transferring the organic waste-slurry to a paddle pulper/finisher, processing the waste-slurry in the paddle pulper/finisher which reduces the particle size of the solids in the waste slurry and separates the waste slurry into a pulp slurry and pomace, and processing the pulp slurry in an anaerobic digester for the production of methane gas fertilizer and soil amendments. In a further process, the organic waste is slurried by dumping the organic waste in a slurry tank, adding a liquid and mechanically mixing the organic waste and liquid until consistent slurry is attained. In a still further process, the slurry from the slurry tank is processed by forming a macerator-slurry in an inline macerator unit which removes heavy solids and cuts other solids into smaller sizes which can be transferred by a slurry pump.

20 Claims, 2 Drawing Sheets

U.S. PATENT DOCUMENTS

| | | |
|---|---|---|
| 5,377,917 A | 1/1995 | Wiljan et al. |
| 5,529,692 A | 6/1996 | Kubler |
| 5,707,417 A | 1/1998 | Yokoyama et al. |
| 5,782,950 A | 7/1998 | Kanitz et al. |
| 6,168,642 B1 | 1/2001 | Valkanas et al. |
| 6,254,775 B1 | 7/2001 | McElvaney |
| 6,296,766 B1 | 10/2001 | Breckenridge |
| 6,299,774 B1 | 10/2001 | Ainsworth et al. |
| 6,342,378 B1 | 1/2002 | Zhang et al. |
| 6,368,500 B1 | 4/2002 | Asa et al. |
| 6,379,505 B1 | 4/2002 | Wiljan et al. |
| 6,454,944 B1 | 9/2002 | Raven |
| 6,464,875 B1 | 10/2002 | Woodruff |
| 6,555,359 B2 | 4/2003 | Cummings |
| 6,569,332 B2 | 5/2003 | Ainsworth et al. |
| 6,824,682 B2 | 11/2004 | Branson |
| 6,905,600 B2 | 6/2005 | Lee, Jr. |
| 2002/0079266 A1 | 6/2002 | Ainsworth et al. |
| 2002/0148778 A1 | 10/2002 | Raven |

OTHER PUBLICATIONS

Vogelsang. "How the Rotacut Works." Vogelsang (Aug. 2006).
Watson-Marlow Bredel Pumbs Ltd. "Watson-Marlow Bredel Pumps—Peristaltic and High-Pressure Hose Pumps." Watson-Marlow Bredel Pumps Ltd., England (Aug. 2006).

* cited by examiner

PROCESS OF TREATING ORGANIC WASTE FOR ANAEROBIC DIGESTION

BACKGROUND OF THE INVENTION

This invention relates to a process and apparatus for treating organic wastes, particularly food wastes to allow a highly biodegradable material to be pumped to anaerobic digesters where they are converted into a fertilizer-type material and renewable energy such as methane gas.

Municipal solid waste collection and disposal is a major world wide problem. Disposal by burial has resulted in serious depletion of suitable sites. Existing dump sites are continuously emitting global warming methane and carbon dioxide gases which are difficult to collect. Many such dump sites, indeed have caused methane fires which are difficult to extinguish. As bottom liners deteriorate, leachate has entered and contaminated the ground water system at many sites. Disposal by incineration has become more questionable as energy prices have increased and contamination of the air has become an increasing problem.

Recognition of the problem has resulted in the development of many processes to convert municipal solid waste into commercially useable products such as soil amendments, fertilizer and methane gas which can be used to produce heat or to generate electricity.

Some of these processes attempt to convert unsorted general municipal waste into commercial products by collecting unsorted waste which may contain, food wastes, paper, cardboard, glass, metal cans, rags, yard waste, farm wastes, food processing plant wastes, wood, metal objects and other wastes too numerous to catalog. Processes which attempt to recycle unsorted municipal wastes are expensive involving many different types of heavy expensive sophisticated equipment, manual labor for sorting, and substantial supplies of fuel and electricity.

SUMMARY OF THE INVENTIONS

The present invention is directed to processing organic wastes, especially food wastes, and other similar biologically degradable wastes which have been segregated from other municipal wastes at the source before they have been mixed together. Sources of such segregated wastes can be found at restaurants, institutional kitchens such as schools, retirement homes, prisons or special food processing facilities such as farms, grocery stores, food canning or food freezing factories.

An object of the present invention is to process presorted food wastes and similar biologically degradable wastes which can be anaerobically digested at a minimum cost in equipment, at a plant requiring minimum real estate and with maximum generation of methane gas, fertilizer and soil amendments.

Another object is to process the wastes using standard commercially available equipment which is low in initial cost, easily and inexpensively maintained and easily and safely operated.

A further object is to use machinery which requires low power requirements thus minimizing ever increasing costs of electricity and energy.

Since even presorted wastes may contain non digestible wastes, another object is to select machinery which can easily and efficiently remove such non digestible material from the feed stock to the digesters. Such items in food waste collected from restaurants for example may include, bottle caps, plastic eating utensils, food wrappers, plastic wrappers, rubber bands, broken glass grit, rocks, and seeds.

Still another object is to process waste which can be fed to an anaerobic digester such as used by many municipalities for waste water and solids treatment without any additional modifications of such anaerobic digesters.

DESCRIPTION OF THE INVENTION

Figure 1:
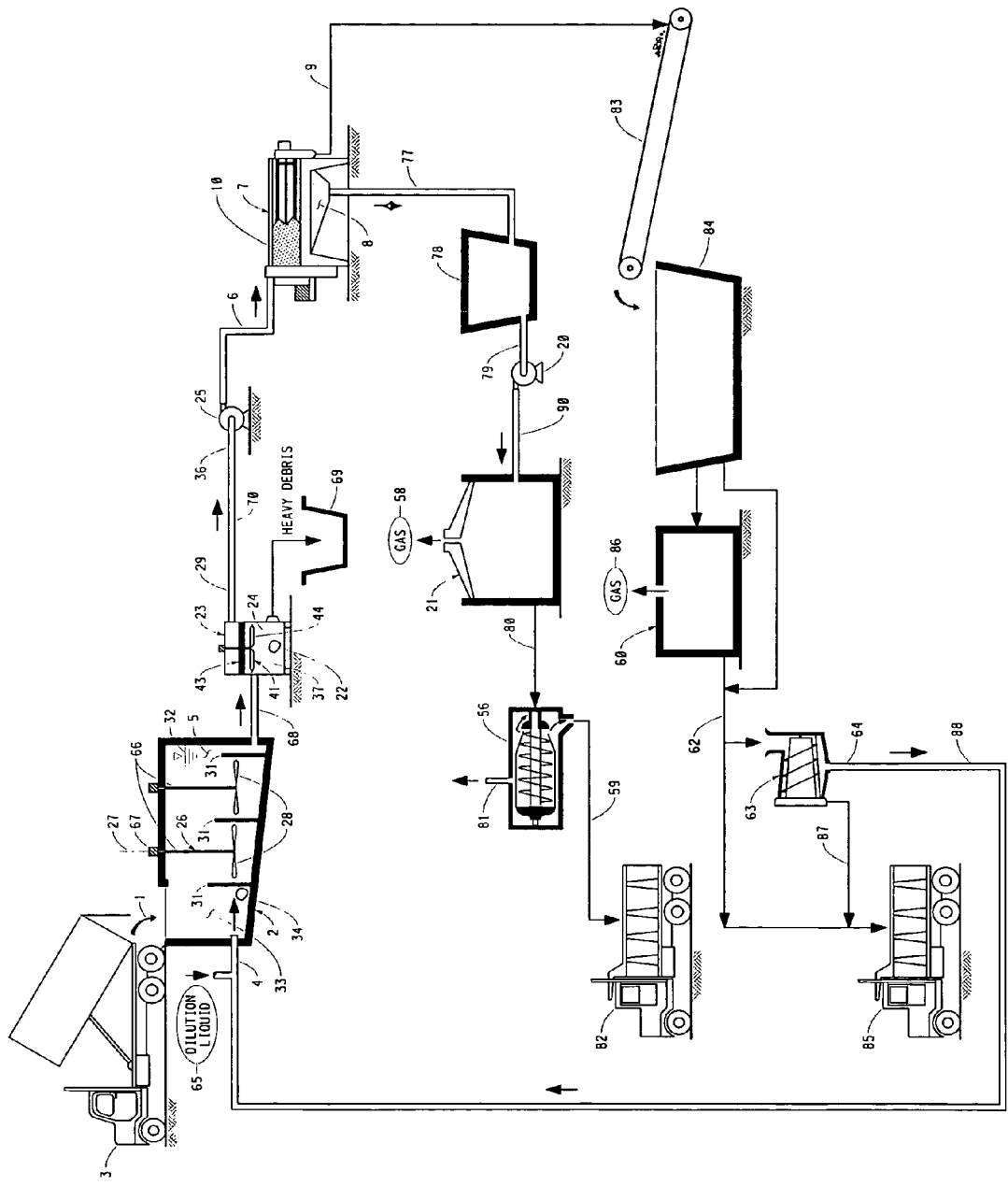
FIG. 1 is a schematic view of the process of the present invention.

The process of the present invention for treating organic waste for anaerobic digestion of biogenic-organic substances, comprises the following process steps: preparing a waste-slurry from organic waste; transferring the waste-slurry to a paddle pulper/finisher 7; forming a finisher-slurry 52 in the paddle pulper/finisher and separating a pulp 8 and a pomace 9 from the finisher-slurry 52 in the paddle pulper/finisher 7, the paddle pulper/finisher 7 having a cylindrical screen body 10 formed with small discreetly spaced openings 11 throughout the body between inlet and outlet end openings 12, and 13; at least one elongated paddle 14 extending a substantial portion of the length of the cylindrical screen body 10 carried on a rotating paddle shaft 15 having an axis 16 concentric with the longitudinal axis 17 of the cylindrical screen 10, and the paddle 14 being formed with a paddle edge 18 positioned in close proximity to the cylindrical screen body 10; the paddle 14 having a pitch 19 for propelling the finisher-slurry 52 toward the outlet opening 13 in screen body 10 while pressuring the finisher-slurry 52 radially outwardly and against the cylindrical screen body 10 thereby reducing the particle size of the finisher-slurry 52 by action of the paddle 14; extruding and forming the pulp 8 exiting through the small screen openings 11, and the pomace 9 exiting the cylindrical screen body 10 through the outlet opening 13; transferring the pulp 8 to an anaerobic digester 21; and digesting the pulp 8 in the anaerobic digester 21.

Referring to FIG. 1, the process previously described the step of preparing the waste-slurry may also include receiving the waste 1 in a slurry tank 2 from a collection/transfer means such as a collection truck 3 or a transfer truck or bin; mixing the waste 1 in the slurry tank 2 with diluting liquid from a diluting liquid source 4; and transferring the waste-slurry with a slurry pumping means 25.

Referring again to FIG. 1, the process as previously described may also have a slurry pumping means which is a positive displacement hose-pump 25 capable of abrasive slurries for transferring the waste-slurry to a paddle pulper/finisher 7.

Figure 3:
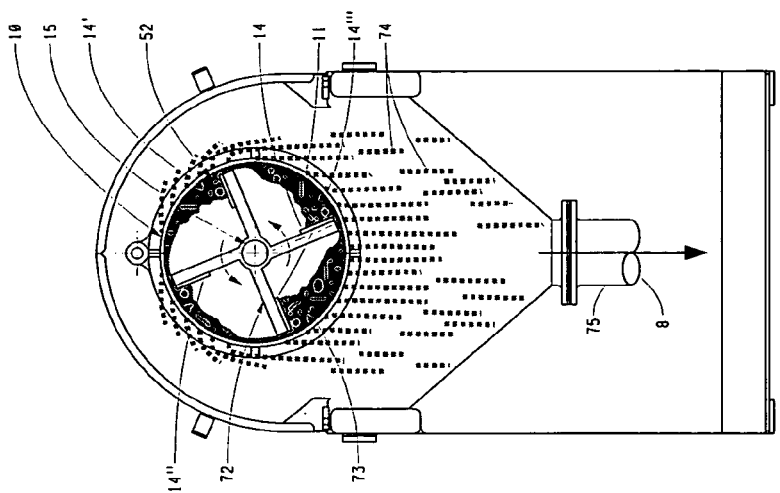
FIG. 3 is a cross section of the machine illustrated in FIG. 2 taken generally along the line 3-3.
Figure 2:
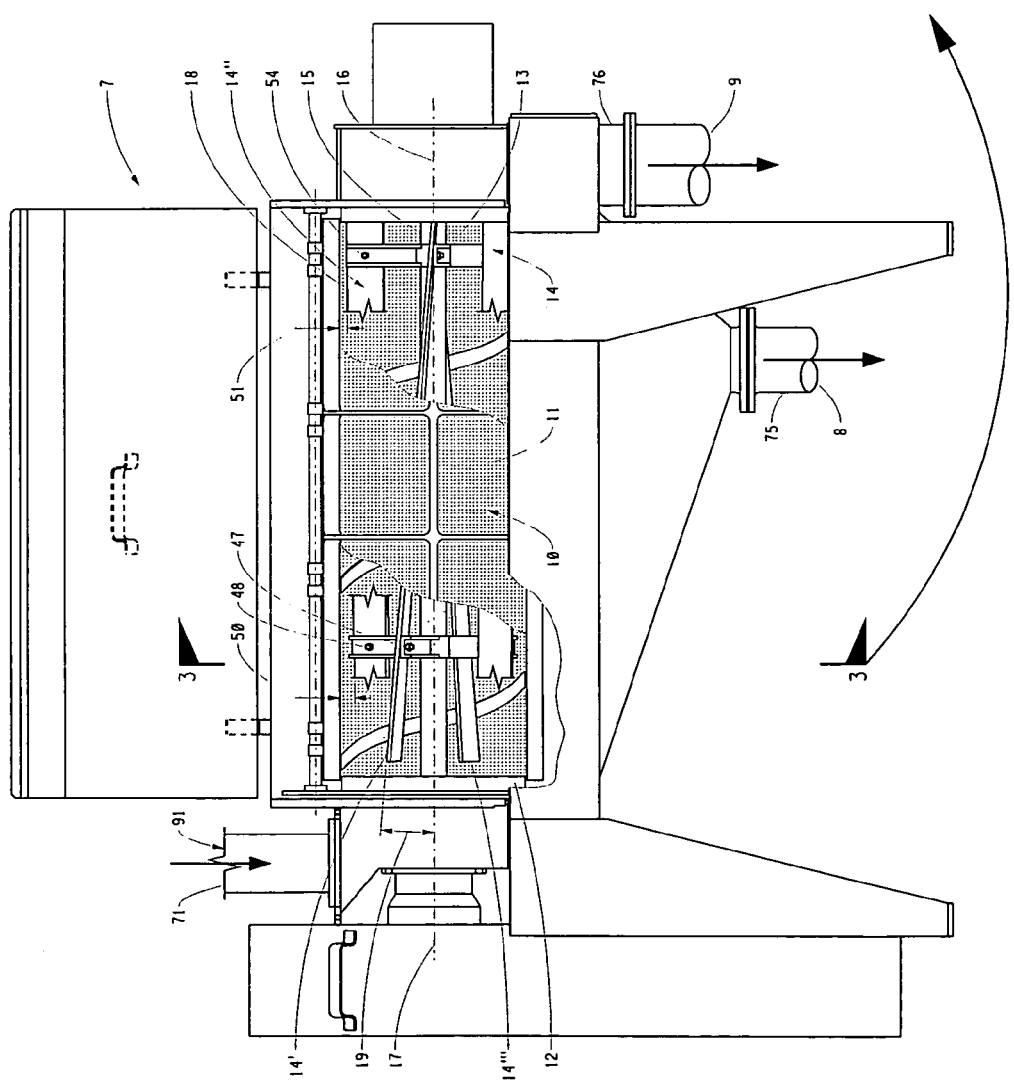
FIG. 2 is side view of a paddle pulper/finisher used in the process of the present invention. Portions of the machine are in cross section to more clearly show the construction of the machine.

Referring to FIGS. 1-3, a preferred form of the invention is shown in which the process of treating organic waste for anaerobic digestion of biogenic-organic substances, includes the following process steps: preparing a waste slurry from organic waste 1 in a slurry tank 2 from a collection/transfer means such as a truck 3 by mixing the organic waste 1 in a slurry tank 2 with diluting liquid from a liquid source 4 to form a slurry-tank slurry 5; forming a macerator-slurry 24 by positioning and operatively connecting an inline macerator unit 23 between and to the slurry tank 2 and a paddle pulper/finisher 7, and separating and removing heavy objects 22 from the macerator-slurry 24, and grinding the remaining macerator-slurry 24 to a predetermined size forming a macerator-finish slurry 29; transferring slurry-tank slurry 5 from the slurry tank 2 to the inline macerator unit 23 by slurry-tank-slurry transfer means such as a pipe; transferring the macerator-finish slurry 29 from the inline macerator unit 23 to the paddle pulper/finisher 7 with a macerator finish slurry transfer means such as a pipe 6; forming a finisher-slurry 52 in the paddle pulper/finisher 7 and separating a pulp 8 and a pomace 9 from the finisher-slurry 52 in the paddle pulper/finisher 7, and the paddle pulper/finisher 7 having a cylindrical screen body 10 formed with small discreetly spaced openings 11 throughout the cylindrical screen body 10 between inlet and outlet end openings 12 and 13; at least one elongated paddle 14 extending a substantial portion of the length of the cylindrical screen body 10 carried on a rotating paddle shaft 15 having an axis 16 concentric with the longitudinal axis 17 of the cylindrical screen body 10 and the paddle 14 is formed with a paddle edge 18 positioned in close proximity to the cylindrical screen body 10; the paddle 14 having a pitch 19 for propelling the finisher-slurry 52 from the inlet opening 12 toward the outlet opening 13 while pressuring the finisher-slurry 52 radially outwardly and against the cylindrical screen body 10 thereby reducing the particle size of the finisher slurry 52 while extruding and forming a pulp 8 exiting through said screen openings 11, and said pomace 9 exiting said cylindrical screen body 10 through the outlet opening 13; transferring the pulp 8 to an anaerobic digester 21; and digesting the pulp 8 in the anaerobic digester 21.

Referring to FIG. 1, in the process as described above, the macerator-finished slurry transfer means may be a macerator-finish slurry pumping means 25.

In another form of the invention, the macerator-slurry pumping means 25 is a positive displacement hose-pump capable of abrasive slurries.

In some instances, partially filling the slurry tank 2 with diluting liquid from diluting liquid source 4 prior to receiving waste 1 will be more efficient in practicing the invention. The mechanical mixers 26 mounted on generally vertical axis 27 having blades 28 can be started and operated before and during the loading of the slurry tank 2 with the waste. Operation of the mechanical mixers should be continued until consistent food waste slurry tank slurry 5 is achieved.

The process may be improved by providing short walls 31 in the base of slurry tank 2 up to about one third the high liquid level height 32 to provide low velocity zones 33 where very heavy materials 34 can settle out and be retained in the slurry tank 2, preventing the very heavy materials 34 from leaving the slurry tank 2 and damaging downstream systems.

Preferably, the process may be optimized by operatively connecting the in line macerator 23 to the suction side 36 of the macerator-finished slurry pumping means 25 to prevent over pressurization of the macerator unit 23 and providing a rock trap 37 for collecting and removing heavy materials 22 such as rocks and metal objects which settle as the velocity of the macerator-slurry 24 slows through the inline macerator unit 23.

In another form of the process, good results may be achieved by adding the step of further reducing the size of remaining solids in the slurry after removal of the heavy materials 22 by means of a cutting assembly 41 in the macerator unit 23 having one or more two-edged cutting blades 42 working against a fixed screen 43 to reduce the solid particles in size so as to pass through the fixed screen 43 with the cutting assembly being capable of two way blade rotational direction to enable larger particles which become trapped in the fixed screen 43 to be severed with a second pass of the blade 42 from an opposite direction and to pass through the fixed screen 43.

In the process described above production may be improved by providing paddle pulper/finisher 7 with two or more paddles 14', 14", and 14'" on paddle shaft 15.

Providing means 47 on the paddle pulper/finisher 7 to change the paddle pitch 19 to vary the rate of conveyance of the pomace 9 through paddle pulper/finisher 7 may be advantageous to increase production. The paddle pitch may be changed depending on the ratio of pulp 8 to pomace 9 or other factors.

The production of the process described above may be improved by providing means 48 on the paddle pulper/finisher 7 for varying the paddle edge clearance 50 of the paddle edge 18 with the cylindrical screen body 10 to vary the pressure of the finisher-slurry 52 against the cylindrical screen body 10.

Providing means 54 in cooperation with means 48 on the paddle pulper/finisher 7 for varying the paddle edge clearance 51 with the cylindrical screen body 10 as a function of the distance from the inlet opening 12 to the outlet opening 13 may be used to reduce the water content of the finisher-slurry as a function of the distance from the inlet opening 12.

Providing means (not shown in the drawings) for varying the rotational paddle speed of the paddles 14 of the paddle pulper/finisher 7 may be provided to optimize pomace 9 throughput and dryness and to vary paddle pressure on the finisher-slurry 52 to improve pulp 8 extrusion through the small discretely spaced openings 11 in cylindrical screen body 10.

Selecting cylindrical screen bodies 10 with different small discretely spaced opening sizes 11 may be carried out to vary the maximum particle size of pulp 8 passing through the small discrete openings 11 in the cylindrical screen body 10 and to vary the minimum size of grit which will be retained in the pomace 9.

In the present application, the digester is preferably a wet anaerobic digester 21 producing a mixture of methane 58 and other gases.

In the present application, preferably dewatering means 56 for dewatering the residual solids from the wet anaerobic digester 21 for producing soil amendments from a cake 59 is provided.

In the present process as described above, the pomace 9 may be processed in a dry digester 60 for producing additional methane gas.

The process of the present invention described above, may include processing the residual dry solids 62 from dry digester 60 by providing a dewatering means 63 for dewatering the residual dry solids 62 and producing a source of diluting liquid 64 for return to the slurry tank 2 provided in the step of preparing a slurry-tank slurry from the organic waste 1.

Source-separated food wastes from restaurants, grocery stores, and other food handling facilities-as well as source-separated food wastes from residential collection is pre-treated to reduce the maximum size of any solids contained in the waste to allow unimpeded pumping of the slurried waste through the process of the present invention. One and a half inches or approximately 3.8 cm is a typical maximum solids diameter; however, larger sizes could be tolerated if so designed. Solids size reduction could be accomplished by a variety of processes singly or in combination, for example: screening, crushing, grinding, or feed mixers. Pretreatment could also include metals removal with a magnetic belt or some other method. Other well known techniques to remove other non-biodegradable materials may also be employed. However, if an organic, biodegradable waste already meets the maximum size requirement, and has relatively low contaminants, no pretreatment is needed.

Source-separated waste typically ranges from 25 to 30% total solids, with about 90% (ranging from 85% to 90%) of the total solids being volatile solids.

Referring to FIG. 1 a brief outline of one commercial form of the process of the present invention is described. Organic waste 1, such as food waste is picked up by a collection truck 3 or other transfer means is picked up and dumped directly into a slurry tank 2 where the food waste is slurried and the total solids content is reduced to approximately 10% (ranging from 5% to 13%, with a typical chemical oxygen demand range of 80,000 to 200,000 mg/L). Dumping directly into a slurry tank 2 instead of dumping waste 1 onto the ground and then picking the waste 1 with a front loader wheeled tractor saves having to obtain certain government permits and reduces the amount of rock and grit that must be removed before delivery to an anaerobic digester 21. Dumping the waste 1 directly into a slurry tank 2 is also preferable to dumping the waste 1 onto a concrete pad which would have to be scrubbed daily to reduce odor contamination and/or the building of an enclosed building which would have to be large enough for a truck to enter the building. If the waste is delivered in a building, the air in the building would have to be scrubbed at additional cost. The receiving-slurry tank can be covered to allow any foul air from the waste to be collected and scrubbed for odor control.

Preferably the slurry tank 2 should be partially filled with diluting liquid prior to the receipt of waste 1. Diluting liquid may be water from a source 65, which could be fully or partially treated municipal wastewater or it may include diluting liquid 64 which may come from the digesters used in the process disclosed in the invention, or it may include some other liquid or liquid waste.

The slurry tank 2 should be partially filled with diluting liquid 65 prior to the dumping of the waste 1 so that mechanical mixing may begin immediately during dumping and continue for a prescribed time depending on the type of waste material itself and the water content of the waste material. Mechanical mixers 26 with propellers 28 may be used to mix the waste. The motors 67 for rotating vertical shafts 66 for rotating propellers 28 need not be high horsepower for the slurry need only be in a form which can be pumped or leave the slurry tank 2 by gravity through pipe 68 in the bottom of slurry tank 2. The mechanical mixers 26 are designed to keep all or almost all of the more heavy materials in the organic waste suspended in the slurry-tank slurry 5 to prevent these materials from settling and accumulating in the receiving slurry tank 2.

Slurry tank 2 may be constructed to separate out the very heavy materials 34. Such separation may be enhanced by building short walls 31 in the base of the slurry tank 2 having a height of about 30% of the high liquid level height 32. The very heavy objects 34 can settle out in the low velocity zones 33 in the slurry tank 2.

Once a consistent slurry-tank slurry 5 is achieved which typically requires less than 30 minutes of mixing in the receiving-slurry tank 2 and where the waste is highly separated or normally contains very little inorganic waste contaminants or non-digestible organic wastes and has a small particle size, the slurry-tank slurry 5 may be dumped or pumped directly into the paddle pulper/finisher 7. In most instances, however, the slurry-tank slurry 5 should be pumped through an inline macerator unit 23 to reduce the amount of heavy materials such as rocks, metal objects, or other heavy materials 22, as well as to chop up fibrous materials, wooden sticks and other materials that could cause pipe and equipment plugging. Inline macerator 23 may also provide a rock trap 37 for heavy objects removal and may be installed between the receiving-slurry tank 2 and the slurry pump 25. This type of inline macerator 23 can reduce the chance of plugging pipes and equipment in the process, and provide a more evenly distributed solids loading to the paddle pulper/finisher 7. The macerator 23 is located on the suction side of the slurry pump 25 to prevent over pressurization of the macerator unit 23, as well as to remove and/or reduce the size of contaminants early in the process to minimize damage to the slurry pump 25 and minimize the likelihood of pipe and equipment blockages. The velocity of the macerator-slurry 24 slows through the inline macerator 23, which allows heavy materials 22 such as rocks and metal objects to settle and collect at the bottom of the macerator 23. The heavy materials 22 can then be removed through a flanged cleanout either manually or through a flushing cycle that introduces an increased water flow to carry the heavy material out of the macerator and into a debris box 69 with a strainer (not shown). The remaining solids in the macerator-slurry 24 are further reduced in size by a cutting assembly that can have anywhere from 2 to 6 cutting blades, with 4 being typical. The two-edged cutting blades work against a fixed screen to reduce the solid particles to a size that will pass through the screen. The cutting blades are made of hardened steel with a minimum Rockwell hardness of 60. The macerator shaft is made of hardened alloy steel. Solids are retained behind the screen until the cutting blades reduce the size to allow passage through the screen. Larger solids can become trapped in the screen and may not be severed with one pass of a blade. This triggers repeated reversals of the blade rotational direction. The result is that the solids are alternately cut from both directions (two adjacent two-edged blades) until it is severed. Screen size openings can vary from 8 to 30 mm. Blade speed ranges from 100 to 300 rpm, which is based on the horsepower requirements resulting from slurry waste loading rates. The design of the cutting blades allows the blades to self sharpen against the screen, and then reverse to use the sharpened side of the blades. The reversing feature also prevents damage from difficult to process materials.

Transfer of the macerator-finish slurry 29 is generally by a pipe 70 which connects with a slurry pump 25. The slurry pump 25 is typically a peristaltic hose pump, capable of pumping highly abrasive slurries, at high flow rates and high pressures. This type of pump is typically used in the mining industry to pump abrasive metal slurries, and is necessary in the present invention because food waste often contains sharp metal pieces, glass shards, grit, and other abrasive materials. The hose pump is also capable of drawing a high suction, up to 27 ft, to allow unimpeded flow through the processes. The pump operates at a variable speed to control pump flow, which typically ranges from 25 to 250 gpm, based on processing a 20-ton food waste load. The pump hose is made of abrasion resistant rubber to minimize wear and tear from glass, metal, and shell fragments found in the food waste slurry. The pump is also capable of run dry operation in the event of line plugging, which is possible with the varied nature of contaminants in the food waste slurry.

The slurry pumping means 25 such as a hose pump conveys the macerator-finish-slurry to the paddle pulper/finisher 7. The paddle pulper/finisher 7 is responsible for removing fibrous materials, grit, metal objects, plastics, fruit pits, and other materials that are non-biodegradable or poorly biodegradable in an anaerobic digester, from the finisher-slurry 52 or food waste slurry. This paddle pulper/finisher 7 is one that is commonly used in the food processing industry. The food processing paddle-finisher is often called a pulper when the screen openings are larger, but even with the larger screen openings this equipment is substantially different than a pulper used in the paper or recycled paper industry. The paddle pulper/finisher 7 operates in a continuous flow-through mode, in contrast to a batch mode, as the receiving-slurry tank 2 is pumped down. The macerator-finish-slurry 29 or feed slurry (as total solids) loading to the paddle pulper/finisher 7 ranges from 5,000 to 7,000 lbs/hour. The solids in the slurry are moved through the paddle pulper/finisher 7 by the paddle assembly, which exerts very high rotational forces against the fixed cylindrical screen body 10. It is critical for the screens to be manufactured of thick steel to minimize damage. The paddles 14 in the paddle pulper/finisher 7 are connected with high-strength stainless steel arms 72 to a shaft 15 that runs length-wise through the center of the cylindrical screen 10. The paddle assembly rotates within the cylindrical screen around the center shaft, and is driven by a V-belt drive, which is driven by a 20-40 hp motor. The speed of the paddle assembly is typically 200-1000 rpm. The paddles 14 have a pitch 19 of approximately 4 inches to aid in conveyance of the slurry and rejected materials through the paddle pulper/finisher. Insufficient paddle pitch will reduce finisher-slurry 52 throughput significantly.

The soft, biodegradable materials in the finisher-slurry 52 are pushed toward the cylindrical screen by the action of the paddle assembly, which operates concentrically within the screen, and are pressured through the small screen openings 11. Larger particles that can not be reduced in size to pass through the small openings 11 in the cylindrical screen 10, stay within the cylindrical screen 10 and are discharged through outlet opening 13 in the cylindrical screen 10 and down a chute or exit port 76 at the end of the paddle pulper/finisher 7. Materials that pass through the screen are called "pulp 8." The materials that do not pass through the screen are called "pomace 9" and are moved out of the paddle pulper/finisher 7 by the paddles 14. The pulp 8 is mostly biodegradable and is pumped to one or more wet anaerobic digesters 21, which accept slurries up to about 15% solids by weight. The pulp 8 is fairly homogeneous in appearance. The TS, VS and COD are comparable to that of the digester slurry feed. The total solids mass recovered in the pulp 8 is approximately 90% of the feed. The COD recovered (on a mass basis) in the pulp 8 is approximately 95%.

The paddle edges 18 of paddles 14 do not actually touch the cylindrical screen 10. Paddles 14 are mounted on paddle arms at a pitch 19 so as to mechanically force the finisher-slurry 52 longitudinally in a spiral motion through the length of cylindrical screen body 10 to the outlet opening 13 in cylindrical screen body 10. At the same time, as shown in FIG. 3, rotation of the paddles 14 about axis 16 of paddle shaft 15, moves the finisher-slurry 52 by centrifugal force against the walls of cylindrical screen body 10 which pressures the liquid and smaller particles through the small discretely dispersed openings 11 where it is extruded as pulp 8. At the same time, paddles 14 build up a mound 73 of finisher slurry 52 in front of each paddle 14. The mound 73 further builds up the pressure on the finisher-slurry 52, forcing the liquid and smaller particles through the small openings 11 in the cylindrical screen 10.

The speed at which the finisher-slurry 52 passes through the cylindrical screen body 10 may be varied by increasing or decreasing the speed at which the paddles 14 are rotated or the pitch 19 of the blades 14 may be varied.

The amount of dewatering that occurs in the paddle pulper/finisher 7 may be varied by varying the distance of the edge 18 of paddle 14 from the cylindrical screen body 10. In addition, the amount of dewatering that takes place can be varied by setting the rear end of the edge 18 of blade 14 a further distance from the cylindrical screen body 10 at the inlet end of the screen than the outlet end of the screen. Thus the finisher-slurry 52 becomes dryer as it progresses through the paddle pulper/finisher 7.

FIG. 3 shows streams 74 of pulp 8 exiting the cylindrical screen body 10 through openings 11 in screen 10 and exiting the paddle pulper/finisher 7 through exit port 75. At the same time pomace 9 passes through the outlet opening 13 in screen body 10 and exits the paddle pulper/finisher 7 through exit port 76.

The pulp 8 may be carried by a pipe 77 to a holding tank 78 where it may be temporarily stored so that it may be continuously moved through an exit pipe 79 under suction by means of pulp pumping means. Pulp 8 is then pumped to a wet anaerobic digester 21 where methane 58 and carbon dioxide gas are produced.

The wet anaerobic digester 21 can be operated in either the mesophilic or thermophilic temperature ranges. The wet anaerobic digester 21 may be one that is used in a wastewater treatment plant, but has additional capacity to take source-separated food wastes or other organic wastes in addition to wastewater treatment plant sludges, or a digester built specifically for food waste digestion.

The anaerobic digester is typically a "wet" digester 21 that accepts slurry-type organic wastes in the range of less than 1% to about 15% total solids content by weight. The anaerobic digestion of the food waste pulp produces a gas 58 consisting mostly of methane and carbon dioxide, and a digestate that typically has a 2-4% total solids content by weight. The digestate is dewatered in a bowl-type centrifuge 56, or some other method of dewatering the digestate. The dewatered portion of the digestate is called the cake 59, and the remaining portion is called the centrate 81 (from centrifuges), filtrate (from filter presses or similar filter processes), or something similar. The cake 59 is typically about 15-30% total solids content by weight, and is hauled away to be beneficially used as a fertilizer-type material on agricultural fields, or alternative daily cover on landfills, or some other use. The centrate 81 is typically sent to some type of wastewater treatment process, or might be used to dilute the food waste in the receiving-slurry tank 2.

The pomace 8 is mostly non-biodegradable, or not well biodegraded in wet digestion systems, especially since the pomace is typically 20%-40% solids by weight. The pomace is either disposed of or anaerobically digested in a dry digester 60, which accepts materials with approximately 20-50% solids by weight. The pomace 8 is heterogeneous in appearance, containing fibrous organics, as well as a wide variety of the food waste slurry contaminants. These contaminants include, but are not limited to: plastics, chop sticks, corks, bottle caps, shells, rags, rubber bands, and fruit labels. The pomace 8 is dry in appearance, with a density ranging from 2.75 to 5 lbs/gallon. Consequently, the pomace is readily compacted if desired to reduce the volume. Pomace 8 ranges from 20 to 30% TS, depending on the paddle pulper/finisher 7 operation, with about 80 to 90% of the TS being VS. COD typically ranges from 100,000 to 300,000 mg/kg. The pomace fraction (on a mass basis) of the trucked source separated food waste 1 ranges from 5 to 15%.

Material throughput and pomace dryness can be optimized by changing paddle pitch 19, paddle tip clearance 50 and 51, number of paddles 14, and paddle speed; as well as screen hole size 11. An example of this is that a food waste slurry throughput was optimized (approximately 125 gallons per minute) when the paddle pitch was at 4½ inches (11.43 cm), the paddle tip clearance ranged from 0.3 to 0.6 inches (7.6 to 15.3 mm), the paddle speed was 600 rpm, and there were four paddles. The screen hole size was 0.045 to 0.060 inches (1.14 to 1.52 mm), which allowed grit materials to be rejected by the screen, in addition to fibrous materials, plastics and other contaminants, and eliminates the need for a separate grit removal process.

A drier pomace is desirable, since more of the biodegradable materials will be transferred from the pomace to the pulp. A drier pomace, however, usually means a lower material throughput through the paddle pulper/finisher. For example, increasing the paddle tip clearance from the cylindrical screen face usually results in a higher material throughput, but a wetter pomace 9.

The moisture content in the finisher-slurry 52 should be gradually decreased throughout the length of the paddle pulper/finisher 7, reaching the desired dryness just prior to reaching the discharge end of the paddle pulper/finisher 7. If a dry pomace is obtained too soon after the feed contacts the paddles 14, this can result in the paddles attempting to force dry pomace through the cylindrical screen body 10, causing excessive solids accumulation in the paddle pulper/finisher 7 and vibration issues, or drive train problems. In particular, this can be a problem when operating with tight paddle clearances 50 and 51 on the order of 0.1."

Pomace 8 that is dried too quickly also suggests that there is additional capacity under the existing operating conditions for higher material throughput. The variables above (tip clearance, pitch, etc.) can be changed to time pomace drying through the finisher and at the same time reduce or increase the material throughput capacity. Alternately, the material throughput can be increased which will also slow pomace 8 drying through the paddle pulper/finisher 7.

Referring to FIG. 1, pomace 9 may be further processed by transferring the pomace 9 to a conveyor belt 83 which carries it to a debris box 84. From the debris box 84 the pomace 9 may be transferred to either a dry digester 60 or to a dewatering device such as a screw press 63 or to a disposal truck 85. The pomace 9 processed through dry digester 60 may produce methane and other gases 86. The solids from dry digester 60 may be transferred directly to a disposal truck 85 or to a screw press 63 where the cake 87 is transferred to disposal truck 85 for disposal or other beneficial use and the liquid 64 is returned to the slurry tank 2 via a pipe 88.

Dry digester 60 may be one that accepts organic wastes with about 20-50% total solids content by weight. The dry digester can be operated at either mesophilic or thermophilic temperatures. Like the wet digester, the dry digester produces a digestate and a gas 86 composed mostly of methane and carbon dioxide. Both the dry digester gas 86 and the wet digester gas 58 can be used as fuel to run internal combustion engines, turbines, fuel cells, or other similar technology to produce electricity.

The paddle pulper/finisher 7 illustrated in FIGS. 1, 2 and 3 and described in the specification and claims of the application may be constructed in accordance with the Model 202 Pulper Finisher made by Brown International Corporation and shown in the 2 page brochure set forth in the Information Disclosure Statement. All information in the Brown International Corporation brochure is herein incorporated by reference in the description of this application.

The inline macerator unit 23 illustrated in FIG. 1 and described in the specification and claims of the application may be constructed in accordance with the RotaCut Inline Grinder made by Vogelsang and shown in the 1 page brochure set forth in the Information Disclosure Statement. All information in the Vogelsang brochure is herein incorporated by reference in the description of this application.

The slurry pumping means 25 illustrated in FIG. 1 and described in the specification and claims of the application may be constructed in accordance with the Bredel peristaltic, high pressure hose pump by Watson Marlow Bredel and shown in the 3 page brochure set forth in the Information Disclosure Statement. All information in the Watson Marlow Bredel brochure is herein incorporated by reference in the description of this application.

We claim:

1. A process of treating organic waste for anaerobic digestion of biogenic-organic substances, comprising the following process steps:
   a. preparing a waste-slurry from said organic waste;
   b. transferring said waste-slurry to a paddle pulper/finisher
   c. forming a finisher-slurry in said paddle pulper/finisher and separating a pulp and a pomace from said finisher-slurry in said paddle pulper/finisher, said paddle pulper/finisher having a cylindrical screen body formed with small discreetly spaced openings throughout said body between inlet and outlet end openings; at least one elongated paddle extending a substantial portion of the length of said cylindrical screen body carried on a rotating paddle shaft having an axis concentric with the longitudinal axis of said cylindrical screen, and said paddle being formed with a paddle edge positioned in close proximity to said cylindrical screen body; said paddle having a pitch for propelling said finisher-slurry toward said outlet opening while pressuring said finisher-slurry radially outwardly and against said cylindrical screen body thereby reducing the particle size of said finisher-slurry by action of said paddle, extruding and forming said pulp exiting through said screen openings, and said pomace exiting said cylindrical screen body through said outlet opening; transferring said pulp to an anaerobic digester; and digesting said pulp in said anaerobic digester.

2. A process as described in claim 1 comprising:
   a. said step of preparing a waste-slurry includes
      (1) receiving said waste in a slurry tank from a collection/transfer means,
      (2) mixing said waste in said slurry tank with diluting liquid; and
   b. said step of transferring said waste-slurry is with a slurry pumping means.

3. A process as described in claim 2 comprising:
   a. said slurry pumping means is a positive displacement hose-pump capable of abrasive slurries.

4. A process as described in claim 1 comprising:
   a. providing said paddle pulper/finisher with two or more paddles on said paddle shaft.

5. A process as described in claim 1 comprising:
   a. providing means on said paddle pulper/finisher to change said paddle pitch to vary the rate of conveyance of said finisher-slurry through said paddle pulper/finisher.

6. A process as described in claim 1 comprising:
   a. providing means on said paddle pulper/finisher for varying the paddle edge clearance with said cylindrical screen body to vary the pressure of said finisher-slurry against said cylindrical screen body.

7. A process as described in claim 1 comprising:
   a. providing means on said paddle pulper/finisher for varying the paddle edge clearance with said cylindrical screen body as a function of the distance from said inlet opening to said outlet opening to reduce the water content of said finisher-slurry as a function of the distance from said inlet opening.

8. A process as described in claim 1 comprising;
   a. providing means for varying said paddle speed to optimize pomace throughput and dryness and to vary paddle pressure on said finisher-slurry.

9. A process as described in claim 1 comprising:
   a. selecting screens with different hole sizes to vary the maximum particle size of said pulp passing through said cylindrical screen body and varying the minimum size of grit which will be retained in said pomace.

10. A process as described in claim 1 comprising:
    a. said anaerobic digester is a wet anaerobic digester for producing a mixture of methane and other gases.

11. A process as described in claim 10 comprising:
    a. dewatering means for dewatering the residual solids from said wet anaerobic digester for producing soil amendments.

12. A process as described in claim 1 comprising:
    a. processing said pomace in a dry digester for producing additional methane gas.

13. A process as described in claim 12 comprising:
    a. processing the residual dry solids from said dry digester by providing a dewatering means for dewatering said residual dry solids and producing a source of diluting liquid for return to a slurry-tank slurry provided in said step of preparing a waste slurry from said organic waste.

14. A process of treating organic waste for anaerobic digestion of biogenic-organic substances, comprising the following process steps:
    a. preparing a waste slurry from said organic waste in a slurry tank from a collection/transfer means by mixing said organic waste in said slurry tank with diluting liquid to form a slurry-tank slurry;
    b. forming a macerator-slurry by positioning and operatively connecting an inline macerator unit between and to said slurry tank and a paddle pulper/finisher, and separating and removing heavy objects from said macerator-slurry, and grinding the remaining macerator-slurry to a predetermined size forming a macerator-finished-slurry;
    c. transferring said slurry-tank slurry from said slurry tank to said macerator unit by slurry-tank-slurry transfer means;
    d. transferring said macerator-finished-slurry from said macerator unit to said paddle pulper/finisher with a macerator-finished slurry transfer means;
    e. forming a finisher-slurry in said paddle pulper/finisher and separating a pulp and a pomace from said finisher-slurry in said paddle pulper/finisher and said paddle pulper/finisher having a cylindrical screen body formed with small discreetly spaced openings throughout said cylindrical screen body between inlet and outlet end openings; at least one elongated paddle extending a substantial portion of the length of said cylindrical screen body carried on a rotating paddle shaft having an axis concentric with the longitudinal axis of said cylindrical screen and said paddle is formed with a paddle edge positioned in close proximity to said cylindrical screen body; said paddle having a pitch for propelling said finisher-slurry from said inlet opening toward said outlet opening while pressuring said finisher-slurry radially outwardly and against said cylindrical screen body thereby reducing the particle size of said finisher slurry while extruding and forming a pulp exiting through said screen openings, and said pomace exiting said cylindrical screen body through said outlet opening; and
    f. transferring said pulp to an anaerobic digester; and
    g. digesting said pulp in said anaerobic digester.

15. A process as described in claim 14 comprising:
    a. said macerator-finished slurry transfer means is a macerator-finished slurry pumping means.

16. A process as described in claim 15 comprising:
    a. said macerator-slurry pumping means is a positive displacement hose-pump capable of abrasive slurries.

17. A process as described in claim 15 comprising:
    a. operatively connecting said inline macerator to the suction side of said macerator-finished-slurry pumping means to prevent over pressurization of said macerator unit and providing a rock trap for collecting and removing heavy materials such as rocks and metal objects which settle as the velocity of said macerator-slurry slows through said inline macerator unit.

18. A process as described in claim 17 comprising:
    a. further reducing the size of remaining solids in said macerator-slurry after removal of said heavy materials by means of a cutting assembly in said macerator unit having one or more two-edged cutting blades working against a fixed screen to reduce the solid particles in size so as to pass through said fixed screen: and
    b. said cutting assembly being capable of two way blade rotational direction to enable larger particles which become trapped in said fixed screen to be severed with a second pass of said blade from an opposite direction and to pass through said fixed screen.

19. A process as described in claim 14 comprising:
    a. said step of preparing a waste slurry from said organic waste includes partially filling said slurry tank with said diluting liquid prior to receiving said waste and providing and operating mechanical mixers mounted on generally vertical axis during the loading of said slurry tank with said organic waste and continuing to operate said mechanical mixers until a consistent organic waste slurry-tank slurry is achieved.

20. A process as described in claim 19 comprising:
    a. providing short walls in the base of said slurry tank up to about one third the high liquid level height thereby providing low velocity zones where very heavy materials can settle out and be retained in the slurry tank, preventing said very heavy materials from leaving said slurry tank and damaging downstream systems.

* * * * *